United States Patent [19]

Mack et al.

[11] Patent Number: 5,523,486
[45] Date of Patent: Jun. 4, 1996

[54] PREPARATION OF ACETOACETARYLAMIDES

[75] Inventors: Karl E. Mack, Wiesbaden; Michael Bohusch, Neu Anspach, both of Germany

[73] Assignee: Hoechst AG, Germany

[21] Appl. No.: 326,100

[22] Filed: Oct. 19, 1994

[30] Foreign Application Priority Data

Oct. 19, 1993 [DE] Germany .................. 43 35 613.13

[51] Int. Cl.[6] ................................. C07C 231/04
[52] U.S. Cl. .............................. 564/200; 564/199
[58] Field of Search ....................... 564/199, 200

[56] References Cited

U.S. PATENT DOCUMENTS 4,129,596  12/1978  Kunstle et al. .................. 564/199

FOREIGN PATENT DOCUMENTS

| 2309514 | 11/1976 | France . |
| 1518881 | 3/1969 | Germany . |
| 2647499 | 4/1978 | Germany . |
| 57-126453 | 8/1982 | Japan . |
| 1541460 | 2/1979 | United Kingdom . |
| 1588027 | 4/1981 | United Kingdom . |

OTHER PUBLICATIONS

Database WPI, Week 8237, Derwent Publications Ltd., Abstract No. 82–77578E of JP 57 126 453, 1982.

*Primary Examiner*—Shailendra Kumar
*Attorney, Agent, or Firm*—Connolly & Hutz

[57] ABSTRACT

A process for preparing acetoacetarylamides of the formula I

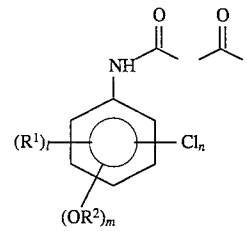

where
$R^1$ and $R^2$ are identical or different alkyl radicals,
l and m are each 0, 1 or 2, and
is 0 or 1,
by addition of diketene to the appropriate arylamine by continuously reacting the arylamine with diketene in the presence of a mixture of water and of a $(C_1-C_4)$-alkanol at temperatures from 60° C. to 100° C. in the course of from 0.1 to 10 min.

21 Claims, No Drawings

PREPARATION OF ACETOACETARYLAMIDES

Acetoacetarylamides are important starting materials in the colorant industry for the synthesis of pigments. The hue and quality of the pigments depends greatly on the purity of the acetoacetarylamides and fluctuations in that purity. There is therefore great interest in acetoacetarylamides of particularly high and consistent purity.

DE-A-1518881 describes the continuous production of acetoacetarylamides from diketene and arylamine in water as reaction medium at temperatures from 0° to 50° C. Owing to the poor solubility of the starting and end-product materials in water, however, there is a great danger— despite the recommended vigorous stirring—of non-uniform reaction and contamination of the products through inclusion of unconverted diketene or arylamine in individual product particles as they form. The 50° C. temperature limit on account of the risk of diketene hydrolysis makes significant solubility effects unlikely even at these elevated temperatures, and it also restricts the rate of the reaction between arylamine and diketene to such an extent that reaction times of 20 to 90 minutes are required. The long reaction times and the technically difficult handling of suspensions appreciably hinder the optimum utilization of this continuous process.

A number of patent documents propose improving the solubility conditions by means of the use of organic solvents, for example toluene or xylene in DE-A-2749327 or alcohols in JP-A2-57-126 453. However, these solvents are frequently such good solvents for the acetoacetarylamides that high yields can for example only be obtained after costly evaporation of the solvent with simultaneous coprecipitation of impurities or else, as in the case of the alcohols, the reaction products have to be isolated by precipitation by addition of water after the reaction. Moreover, the cited laid-open Japanese document in particular is silent on the question of a continuous procedure, probably on account of the likewise limited reaction temperature of 60° C. and the attendant long reaction time of generally more than 60 min.

In view of these restrictions and disadvantages, there is a great need for an improved process whereby the disadvantages of existing processes are avoided and good to very good yields, a high degree of purity and shortened reaction times are made possible. A continuous process, having a high space-time yield (amount of product produced per unit time per unit reactor volume), would offer economic advantages and, owing to small apparatus dimensions combined with correspondingly small retention volumes, safety advantages in the case of highly reactive starting materials.

This object is achieved by a process for preparing acetoacetarylamides of the formula I

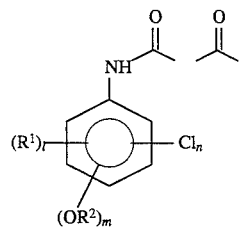

where
R$^1$ and R$^2$ are identical or different alkyl radicals,
l and m are each 0, 1 or 2, and
n is 0 or 1,
by addition of diketene to the appropriate arylamine by continuously reacting the arylamine with diketene in the presence of a mixture of water and of a (C$_1$–C$_4$)-alkanol at temperatures from 60° C. to 100° C. in the course of from 0.1 to 10 min.

The arylamines used can each carry up to two alkyl or alkoxy groups. Of particular interest is the reaction of alkyl or alkoxy compounds which contain in each case up to three carbon atoms in the alkyl radical and represent methyl, ethyl, n-propyl or isopropyl. Of particular importance is the reaction of aniline, 2-methylaniline, 2,4-dimethoxyaniline, 4-isopropylaniline, 2-methoxyaniline, 4-ethoxyaniline, 2,4-dimethylaniline, 2,5-dimethoxyaniline, 2-chloroaniline and 4-chloro-2,5-dimethoxyaniline.

The amines can be used in technical grade quality; solid amines can be water-moist.

Diketene can likewise be used in technical grade quality. It is advantageous to use it in an excess from 3 to 30 mol %, in particular from 5 to 25 mol %.

The alcohol used can be methanol, ethanol, n-propanol, isopropanol or a butanol. It is in many cases advisable to use alcohols which are miscible with water in any proportion, such as methanol, ethanol and the propanols. Ethanol is preferred for occupational hygiene reasons.

The alcohol is always used mixed with water. There is a complex relationship governing the ratio of alcohol to water, the amount of this mixture relative to the individual arylamines, and the maximum reaction temperature, i.e. the boiling point of the alcohol-water mixture.

The water content of the alcohol-water mixture and its amount relative to the arylamine are determined for product purity reasons by the requirement that, on the one hand, the—if necessary, hot—solution should have a very high concentration and that, on the other, the acetoacetarylamide present after the reaction should remain in solution at the reaction temperature. Suitable alcohol-water mixtures are generally characterizable by their boiling temperature from about 70° to 100° C. In the case of ethanol being used, the boiling point of the mixture is advantageously from about 80° to 90° C., corresponding to a water content from about 20 to 80% by weight. It is advantageous, for example, when liquid arylamines such as 2,4-dimethylaniline are used, to have a water content of about 70% by weight, while in the case of solid arylamines such as 4-chloro-2,5,-dimethoxyaniline it is advantageous to have a water content of about 50% by weight.

The weight ratio of amine to alcohol-water mixture can generally vary within the range from 1:1 to 1:20. A range from about 1:1 to 1:15 in particular from 1:1 to 1:10, is advantageous.

The reaction temperature should be at least 60° C. to ensure sufficiently rapid reactions; but 70° C. is generally better. Owing to the instability of the diketene and owing to the boiling temperature of water, 100° C. should not be exceeded as maximum reaction temperature; for safety reasons, a maximum temperature of 95° C. is to be preferred. The optimum reaction temperature for the individual arylamines depends crucially on their reactivity and has to be experimentally determined for each amine. Within the convenient temperature range from 70° to 95° C., the range from 75° to 90° C. is advantageous; in the case of ethanol being used with a water content of from 50 to 70% by weight, temperatures from 83° to 86° C. are favorable.

The setting and limiting of the temperature of the strongly exothermic reactions is subsequently effected—following the initiation phase under autogenous heating, but if desired also under external heating—by cooling the reaction mixture by means of external cooling; by precooling the feed streams; or by increasing the amount of the alcohol-water mixture to such an extent that its heat capacity is able to absorb the evolved heat of reaction to the desired temperature.

An advantage of the novel process is the reaction at the boiling temperature of the alcohol-water mixture and the cooling by condensing the vapors of alcohol and water. The result is technically simple and safe cooling with accurate limitation of the temperature.

The continuous reaction of diketene and arylamine should ideally be carried out with time at high temperature kept to a minimum, the reaction time being taken to be the average mean residence time in the reactor. It should be below about 10 min. Given sufficiently effective heat removal, for example through evaporative cooling, appreciably shorter residence times, for example from about 0.5 to 5 min., can be achieved. A favorable reaction time in the case of the reactions of, for example, 2,4-dimethylaniline, of 2-methoxyaniline or of 4-chloro-2,5-dimethoxyaniline in the presence of ethanol having a water content of 70 or 50% by weight has a duration of from 0.75 to 3 minutes, in particular of about one minute.

Notwithstanding the optimization of the quantities of the starting materials used, isolation of the acetoacetarylamide leaves some of the product in the mother liquor, according to its solubility° The highly selective reaction of the novel process makes it possible to recirculate the mother liquor for reaction repeatedly without significant loss of product quality and in this way to substantially recover the amount of acetoacetarylamide otherwise remaining in the mother liquor. For every recirculation the mother liquor is replenished with a fresh alcohol-water mixture which, in terms of quantity, corresponds to the amount of mother liquor which has remained as moisture in the isolated crude product and is subsequently removed by washing.

Suitable reactors include apparati in which, on the one hand, intensive mixing of the starting components is possible, for example by stirring, by mixing in pumps or by static mixers or else multimaterial nozzles, on the other hand, effective indirect cooling or evaporative cooling must be ensured.

Suitable reactors include for example stirred kettles or stirred kettle cascades, static mixers with a downstream flow pipe, or a rotary pump mixer in line with a circulatory evaporator or a falling-film or thin-film evaporator.

The continuous metering of arylamine and diketene into the reactor always takes place separately, while that of the alcohol-water mixture or of recirculated mother liquor can either take place separately or together with the arylamine. The continuous discharge of the reaction mixture is either by pump or—more simply—by overflow syphon.

The reaction generally takes place under atmospheric pressure. Superatmospheric pressure is associated in the case of the use of evaporative cooling with an increase in the reaction temperature and only of limited use from the safety aspect. Working under reduced pressure can be advantageous in combination with particular alcohol-water mixtures, owing to the solubility requirements, and in connection with an advantageous lowering of the boiling temperature.

Catalysts are generally not required in the reaction, but can be used in known manner to further speed up the reaction. Suitable catalysts include protic acid, for example acetic acid, amines such as triethylamine or else ammonium compounds. Other additions such as color-lightening substances are generally not necessary, although it is advantageous in particular cases, for example in the case of the use of solid amines which have a dark color in solution, to add small amounts, for example of dithionite, in the course of the production process.

The workup of the product stream continuously removed from the reactor is effected in known manner by cooling and crystallization of the acetoacetarylamides. The products are obtained in the highly crystalline state and, owing to their coarse particle size, are simple and quick to isolate by filtration. The mother liquor obtained can generally be re-used in the synthesis to improve the product yield.

The crude product obtained is washed, for example with alcohol-water, to remove mother liquor, and the purified product is if necessary dried or freed of adherent alcohol by gentle distillation in an aqueous suspension, and isolated as a water-moist product.

Following distillative recovery of alcohol-water, the novel process proceeds without producing waste water.

The advantages of the novel process are the small reactors required for the reaction owing to high space-time yields of up to 20 kg of product/1×hour and the associated enhanced work safety due to low retention volumes of the highly reactive diketene. It is further possible to prepare the acetoacetarylamides as generally highly crystalline, readily isolable products in a high purity suitable for the field of pigments. In addition, the recirculation of product-containing mother liquor into the synthesis, which is an important feature of the novel process, ensures an optimum product yield of up to 98% (based on arylamine) and, through simple distillate recovery of aqueous alcohol from workup streams, makes possible the avoidance of waste waters.

The Examples which follow illustrate the invention.

EXAMPLE 1

2.48 kg/h (20.5 mol/h) of 2,4-dimethylaniline, 1.83 kg/h (21.3 mol/h) of diketene (purity 98%) and 8 kg/h of a mixture of 2.4 kg/h of ethanol and 5.6 kg/h of water are metered separately but simultaneously into a reactor which has been preheated to about 80° C. The reactor consists of a double-shell glass vessel of about 0.6 l capacity and is equipped with a stirrer, thermometer, reflux condenser and, at the bottom, with a run-off. Immediately the metering has started, the heat evolved by the reaction causes the reactor contents to reflux at about 85° C. The heating of the reactor is discontinued and the reaction is continued by limiting the reactor contents to about 0.3 l by continuous pumping out. The reactor discharge is cooled to about 15° C. with stirring, and the light-colored crystals which are formed are separated from about 7 kg/h of the pale yellow mother liquor by filtration. The moist product, which is obtained at about 5 kg/h, is washed with about 4 kg/h of cold aqueous 30% strength ethanol and dried, leaving 4 kg/h (19.5 mol/h) of 2',4'-dimethylacetoacetanilide (melting point about 89° C.) corresponding to a yield of 95% based on amine.

To re-use the mother liquor obtained at about 7 kg/h, it is made up with about 1 kg/h of aqueous, 30% strength ethanol to 8 kg/h and reacted with 2,4-dimethylaniline and diketene as described above and worked up to 4.08 kg/h of product (yield 97%).

EXAMPLE 2

2.48 kg/h of 2,4-dimethylaniline, 1.83 kg/h of diketene (purity 98%) and 9 kg/h of aqueous 30% strength ethanol are metered separately but simultaneously at about 20° C. into a reactor which consists of a static mixer (about 0.5 ml; Sulzer) and a downstream flow tube having a capacity of about 0.2 l and a diameter of 6 mm. The flow tube does not contain any internal fitments, is provided with external temperature sensors and is thermally insulated by insulating material. The heat of reaction causes a temperature profile to develop along the flow tube, resulting in temperature of about 78° C. about halfway along the tube. The reactor discharge is cooled to about 15° C. with stirring and worked up as described in Example 1. The yield of 2',4'-dimethylacetoacetanilide is 93.5% based on the amine used. Reusing the about 8 kg/h of mother liquor obtained, making up to 9 kg/h with about 1 kg/h of aqueous 30% strength ethanol and reacting with 2,4-dimethylaniline and diketene as described above raises the yield of 2',4'-dimethylacetoacetanilide to 96.5% without deterioration in the quality of the product (melting point about 89° C.).

EXAMPLE 3

2.4 kg/h (19.5 mol/h) of 2-methoxyaniline, 1.98 kg/h (23.1 mol/h) of diketene (purity 98%) and 6.9 kg/h of aqueous 30% strength ethanol are reacted separately but simultaneously as described in Example 1. The product stream of about 0.3 l, produced under reflux at about 85° C. and kept to a constant volume by pumping out, is cooled down to about 15° C., and the reaction product is crystallized out and separated from the 5.8 kg/h of mother liquor by filtration. The light-colored solids are washed with 5.8 kg/h of aqueous 30% strength ethanol and dried, leaving 3.8 kg/h (18.3 mol/h) of 2'-methoxyacetoacetanilide, corresponding to 94% of yield based on amine. The purity of the product is better than 99.5%.

To re-use the mother liquor, it is made up to 6.9 kg/h with the 1.1 kg/h of product wash liquor obtained and reacted with amine and diketene in the above ratio. The yield of 2'-methoxyacetoacetanilide increases to 97% without loss of quality.

EXAMPLE 4

2.6 kg/h (24.3 mol/h) of 2-methylaniline, 2.4 kg/h (28 mol/h) of diketene (purity 98%) and 7.2 kg/h of aqueous 30% strength ethanol, 6 kg/h of which are replaced in the subsequent reaction cycles by mother liquor, are made to react separately but simultaneously as in Example 1 by limiting the reaction volume to 0.4 l by continuous pumping out. After the reactor discharge has been cooled to about 15° C., the reaction product, which has crystallized out, is separated from the mother liquor, which is to be recirculated into the reaction, washed with about 4 kg/h of aqueous, 30% strength ethanol, and dried. With recirculation of the mother liquor the yield of 2'-methylacetoacetanilide (melting point 105° C.) is 4.5 kg/h, corresponding to a yield of 96.5% based on amine.

EXAMPLE 5

3.6 kg/(19.2 mol/h) of 4-chloro-2,5-dimethoxyaniline are dissolved in 13.5 kg/h of aqueous 50% strength ethanol, 11 kg/h of which are replaced in subsequent reaction cycles by mother liquor product, by heating. The solution, which is at about 80° C., is metered into the reactor of Example 1 with the simultaneous metering of 2 kg/h (23.3 mol/h) of diketene (purity 98%). The reaction mixture, which boils vigorously under reflux at about 85° C., is limited to a volume of about 0.4 l by continuous pumping out. The reactor discharge is cooled and, directly prior to attainment of the crystallization temperature of about 55° C., admixed with small amounts of an about 10% strength aqueous solution of dithionite to obtain a spontaneous lightening in the color of the reddish-brown reactor discharge and thus to obtain light-colored crystals. After further cooling down to about 15° C., filtration of the crystalline product to remove mother liquor, washing with 50% strength aqueous ethanol and drying gives with mother liquor recycling 5 kg/h (18.4 mol/h) of coarsely crystalline 4'-chloro-2',5'-dimethoxyacetoacetanilide (melting point 105°–106° C.) in a yield of 96% based on amine.

What is claimed is:

1. A process for preparing acetoacetarylamides of the formula I

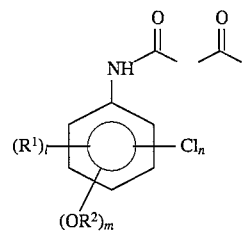

where $R^1$ and $R^2$ are identical or different alkyl radicals, l and m are each 0, 1 or 2, and n is 0 or 1, by addition of diketene to the appropriate arylamine by continuously reacting the arylamine with diketene in the presence of a mixture of water and of a $(C_1$–$C_4)$-alkanol at temperatures from 60° C. to 100° C. in the course of from 0.1 to 10 min.

2. The process of claim 1, wherein $R^1$ and $R^=$ are identical or different $(C_1$–$C_3)$-alkyl radicals.

3. The process of claim 1, wherein the arylamine used is aniline, 2-methylaniline, 2,4-dimethoxyaniline, 4-isopropylaniline, 2-methoxyaniline, 4-ethoxyaniline, 2,4-dimethylaniline, 2,5-dimethoxyaniline, 2-chloroaniline or 4-chloro-2,5-dimethoxyaniline.

4. The process of claim 1, wherein the diketene is used in an excess of from 3 to 30 mol %.

5. The process of claim 1, wherein the water-alcohol mixture has a boiling point from 70° C. to 100° C.

6. The process of claim 1, wherein the alcohol used is methanol, ethanol or propanol.

7. The process of claim 1, wherein the alcohol used is ethanol and the mixture contains between 20 and 80% by weight of water.

8. The process of claim 1, wherein the weight ratio of amine to alcohol-water mixture is from 1:1 to 1:20.

9. The process of claim 1, wherein the reaction is carried out in the course of from 0.5 to 5 minutes.

10. The process of claim 1, wherein the reaction temperature is from 70° to 95° C.

11. The process of claim 1, wherein the arylamine and diketene are metered separately.

12. The process of claim 1, wherein the mixture of alcohol and water comprises recycled mother liquor.

13. The process of claim 1, wherein the heat evolved in the course of the reaction is removed by evaporation of the mixture of alcohol and water.

14. The process of claim 1, wherein the process is carried out at atmospheric pressure, superatmospheric pressure or reduced pressure.

15. The process as claimed in claim 4, wherein the diketene is used in an excess of from 5 to 25 mol %.

16. The process of claim 6, wherein the alcohol used is ethanol.

17. The process of claim 8, wherein the weight ratio of amine to alcohol-water is from 1:1 to 1:15.

18. The process of claim 8, wherein the weight ratio of amine to alcohol-water is from 1:1 to 1:10.

19. The process of claim 9, wherein the reaction is carried out in the course of from 0.75 to 3 minutes.

20. The process of claim 10, wherein the reaction temperature is from 75° to 90° C.

21. The process of claim 14, wherein the process is carried out at atmospheric pressure.

* * * * *